US008675058B2

(12) United States Patent
Donomae et al.

(10) Patent No.: US 8,675,058 B2
(45) Date of Patent: Mar. 18, 2014

(54) ELECTRONIC ENDOSCOPE APPARATUS

(75) Inventors: Yoshifumi Donomae, Kawasaki (JP);
Kazunori Abe, Saitama (JP)

(73) Assignees: Fujinon Corporation, Saitama-Shi (JP);
FUJIFILM Corporation, Tokyo (JP)

( * ) Notice: Subject to any disclaimer, the term of this patent is extended or adjusted under 35 U.S.C. 154(b) by 2127 days.

(21) Appl. No.: 11/253,633

(22) Filed: Oct. 20, 2005

(65) Prior Publication Data
US 2006/0087557 A1 Apr. 27, 2006

(30) Foreign Application Priority Data

Oct. 20, 2004 (JP) ................. 2004-305023

(51) Int. Cl.
G06K 9/22 (2006.01)
H04N 7/18 (2006.01)
G06K 15/02 (2006.01)
H04N 1/107 (2006.01)

(52) U.S. Cl.
CPC .............. *G06K 15/02* (2013.01); *H04N 1/107* (2013.01)
USPC ............... 348/71; 358/1.9; 358/505; 382/313

(58) Field of Classification Search
USPC .......... 600/118, 127; 358/1.19, 1.9, 505, 513, 358/473, 474, 482; 348/71, 68, 65, 45, 46, 348/72; 382/313, 314
See application file for complete search history.

(56) References Cited

U.S. PATENT DOCUMENTS

| 4,827,908 | A | | 5/1989 | Matsuo |
| 5,627,583 | A | | 5/1997 | Nakamura et al. |
| 5,864,361 | A | * | 1/1999 | Sekiya et al. ................ 348/68 |
| 5,871,439 | A | | 2/1999 | Takahashi et al. |
| 6,059,719 | A | * | 5/2000 | Yamamoto et al. ........... 600/127 |
| 6,436,032 | B1 | * | 8/2002 | Eto et al. ................ 600/117 |
| 6,563,602 | B1 | * | 5/2003 | Uratani et al. ............... 358/1.9 |
| 6,717,609 | B2 | * | 4/2004 | Sugimoto et al. ............. 348/74 |

(Continued)

FOREIGN PATENT DOCUMENTS

| EP | 0669756 A1 | 8/1995 |
| JP | 63240826 A | 10/1988 |

(Continued)

OTHER PUBLICATIONS

European Search Report corresponding to European Patent Application No. EP 05022919.4, dated Aug. 30, 2010.

(Continued)

*Primary Examiner* — Jerome Grant, II
(74) *Attorney, Agent, or Firm* — Sughrue Mion, PLLC

(57) ABSTRACT

An electronic endoscope apparatus includes a connection unit for selectively connecting a plurality of machine types of electronic endoscopes which use different color information obtainment methods and a plurality of replacement tables which are provided for the plurality of machine types of electronic endoscopes respectively, and each of which stores a correspondence between values representing colors which can be obtained by each of the electronic endoscopes by photographing an observation object and values representing the true colors of the observation object. The electronic endoscope apparatus distinguishes the machine type of the electronic endoscope and replaces the values of obtained colors by using the replacement table for the distinguished machine type. Further, the electronic endoscope apparatus stores setting information for each purpose of examination, and further performs image processing, based on selected setting information, on the image of which the values of the colors have been replaced.

9 Claims, 10 Drawing Sheets

(56) References Cited

U.S. PATENT DOCUMENTS

| | | | |
|---|---|---|---|
| 7,319,781 B2 * | 1/2008 | Chen et al. | 382/128 |
| 7,492,388 B2 * | 2/2009 | Odlivak et al. | 348/65 |
| 7,613,335 B2 * | 11/2009 | McLennan et al. | 382/128 |
| 2002/0120179 A1 * | 8/2002 | Abe | 600/118 |
| 2002/0131652 A1 * | 9/2002 | Yoda | 382/309 |
| 2003/0025789 A1 | 2/2003 | Saito et al. | |
| 2003/0063188 A1 | 4/2003 | Takahashi et al. | |
| 2003/0071894 A1 * | 4/2003 | Higuchi et al. | 348/65 |
| 2003/0219155 A1 * | 11/2003 | Azuma et al. | 382/156 |
| 2004/0000335 A1 | 1/2004 | Kopel | |
| 2005/0020879 A1 | 1/2005 | Suzuki | |
| 2005/0024658 A1 * | 2/2005 | Ota et al. | 358/1.9 |
| 2005/0036668 A1 * | 2/2005 | McLennan et al. | 382/128 |
| 2010/0156921 A1 * | 6/2010 | McLennan et al. | 345/589 |
| 2010/0228513 A1 * | 9/2010 | Roth et al. | 702/94 |
| 2011/0029733 A1 * | 2/2011 | Adler et al. | 711/115 |

FOREIGN PATENT DOCUMENTS

| | | |
|---|---|---|
| JP | 1113018 | 5/1989 |
| JP | 6304135 A | 11/1994 |
| JP | 2003-204932 A | 7/2003 |
| JP | 2004000335 A | 1/2004 |

OTHER PUBLICATIONS

Japanese Office Action, issued Apr. 19, 2011 in JP 2005-305262.
European Office Action Application No. 05022919.4-1905; Jun. 5, 2013.

* cited by examiner

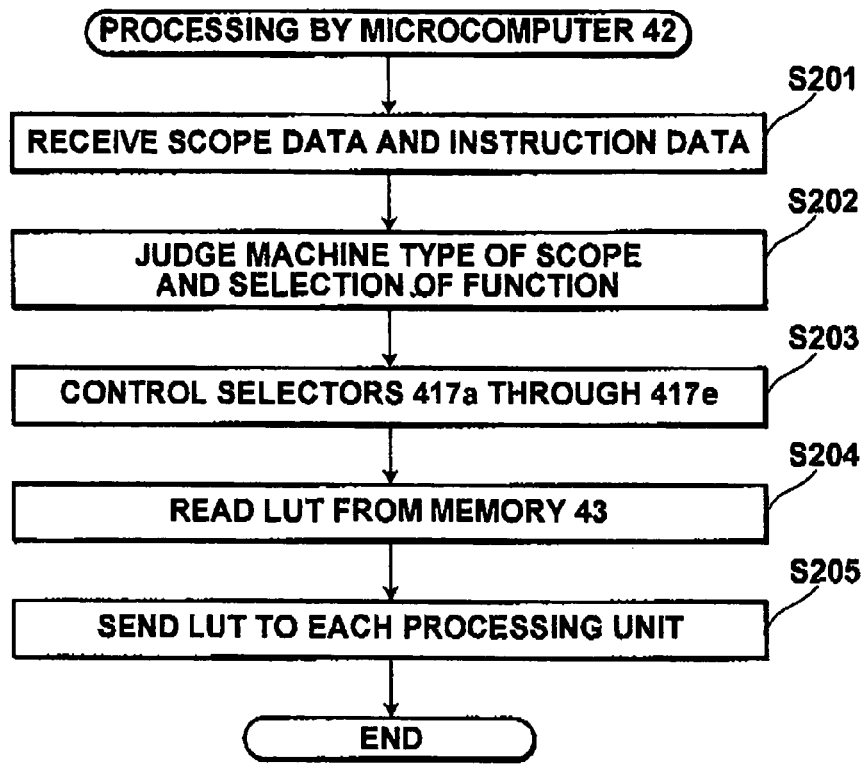
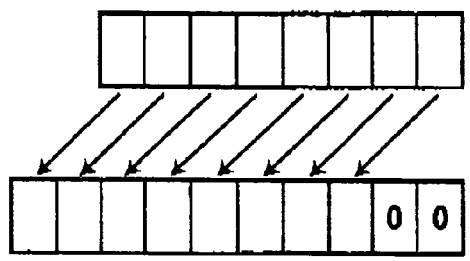

FIG.6

| (R,G,B) | (R',G',B') |
|---|---|
| (0,0,0) | (0,0,0) |
| (1,0,0) | (1,0,0) |
| (2,0,0) | (2,0,0) |
| ⋮ | ⋮ |
| (196,37,3) | (201,30,1) |
| ⋮ | ⋮ |
| (1023,1023,1022) | (1023,1023,1022) |
| (1023,1023,1023) | (1023,1023,1023) |

| (R,G,B) | (R',G',B') |
|---|---|
| (0,0,0) | ⋮ |
| (32,0,0) | ⋮ |
| (64,0,0) | ⋮ |
| ⋮ | |
| (0,32,0) | ⋮ |
| (0,64,0) | ⋮ |
| ⋮ | |
| (0,0,32) | ⋮ |
| (0,0,64) | ⋮ |
| ⋮ | ⋮ |

6

FIG.8
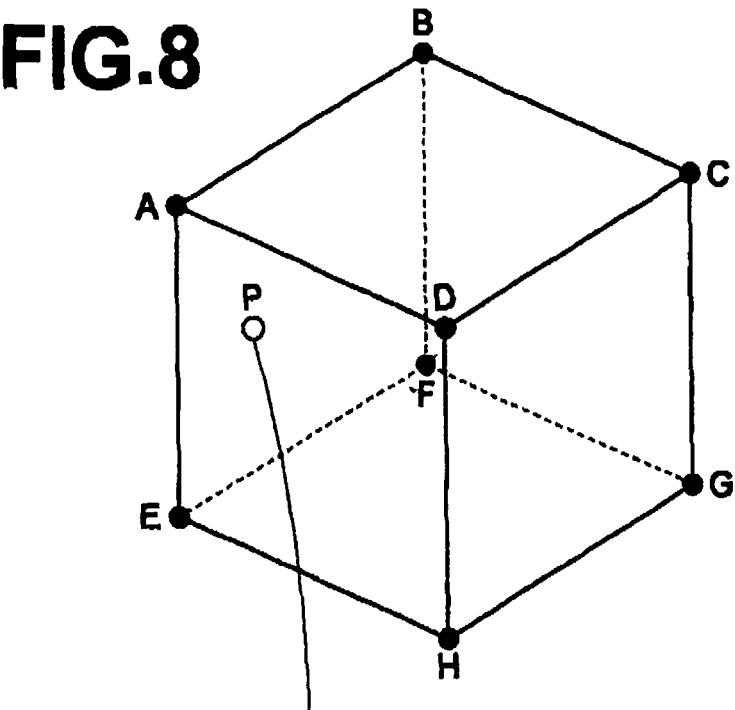
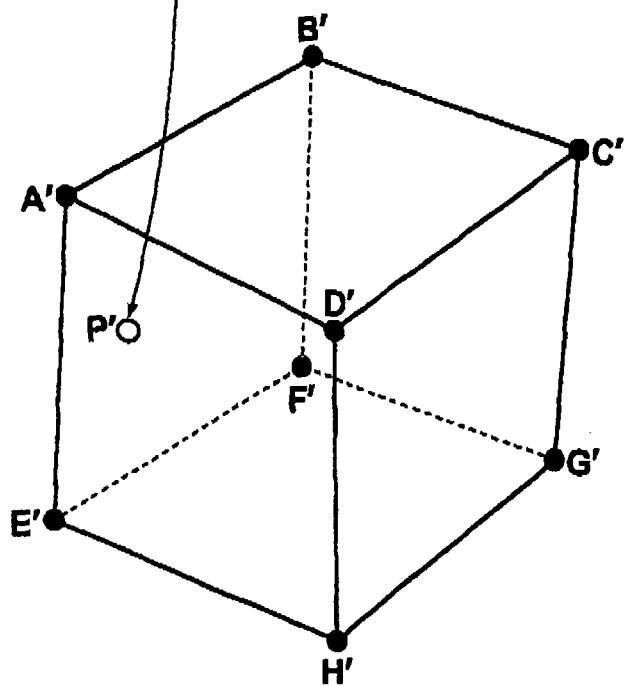

ELECTRONIC ENDOSCOPE APPARATUS

BACKGROUND OF THE INVENTION

1. Field of the Invention

The present invention relates to an image processing function of an electronic endoscope apparatus.

2. Description of the Related Art

An electronic endoscope apparatus is normally provided as a set of a plurality of electronic endoscopes which have different thicknesses and resolutions from each other and a processing apparatus which performs processing on images obtained by endoscopy so that the images become appropriate for output at a monitor. Therefore, it is necessary that the processing apparatus can perform processing on images obtained by each of the electronic endoscopes of the same electronic endoscope apparatus so as to output images which have appropriate qualities at the monitor.

As an invention for solving the problem as described above, an apparatus which has a function of restricting an image zoom function based on the number of pixels of a CCD (Charge Coupled Device) of an electronic endoscope by detecting the type of the CCD at the processing apparatus is disclosed in U.S. Patent Application Publication No. 20050020879, for example.

Further, the processing apparatus of the electronic endoscope apparatus normally has an image processing function for improving the qualities of images. The apparatus disclosed in U.S. Patent Application Publication No. 20050020879 also has a color tone adjustment circuit and a structure enhancement circuit.

As described above, the conventional electronic endoscope apparatus includes a processing apparatus and a plurality of kinds of electronic endoscopes. In the electronic endoscope apparatus, the same type of CCD (Charge Coupled Device) produced by the same manufacturer is mounted on each of the electronic endoscopes, and only the resolution of the CCD is different from each other.

However, the inventor of the present invention or the like is considering mounting CCD's which are produced by different manufacturers from each other, and which use different kinds of color filters from each other. If such CCD's are mounted, the color obtainment methods of the CCD's are different from each other.

However, although the kind of the CCD is judged in the apparatus disclosed in U.S. Patent Application Publication No. 20050020879, the result of judgment is not used in the color tone adjustment circuit of the apparatus. Under the circumstance as described above, it was not necessary to adjust the brightness level or color of an image based on the kind of the CCD. Further, more complex processing is required to adjust the color compared with processing for adjusting the number of pixels. Therefore, an electronic endoscope apparatus which has a function of adjusting the color has not been provided.

SUMMARY OF THE INVENTION

In view of the foregoing circumstances, it is an object of the present invention to provide an electronic endoscope apparatus which can always output a high-quality image which is appropriate for diagnosis at a monitor regardless of the color obtainment method of the CCD. Further, it is an object of the present invention to output the high-quality image without causing users of the electronic endoscope apparatus to perform adjustment.

To solve the problems as described above, the present invention provides an electronic endoscope apparatus which includes an electronic endoscope and a processing apparatus which performs processing on an image obtained by the electronic endoscope. The processing apparatus is configured as described below.

The processing apparatus includes a connection unit which can selectively connect a plurality of machine types of electronic endoscopes which use different color information obtainment methods from each other.

Further, the processing apparatus includes a plurality of replacement tables, each of which is provided for each of the machine types of electronic endoscopes, and each of which stores a correspondence between values representing colors which can be obtained by each of the electronic endoscopes by photographing an observation object and values representing the true colors of the observation object. The replacement tables are stored in a memory or the like in the processing apparatus.

The processing apparatus further includes a machine type distinction means for distinguishing the machine type of an electronic endoscope connected to the processing apparatus by obtaining information representing the machine type of the electronic endoscope from the electronic endoscope.

The processing apparatus further includes a faithful-color-reproduced image production means for producing an image in which the true colors of the observation object are faithfully reproduced by replacing the values of colors obtained by the electronic endoscope connected to the processing apparatus by using the correspondence stored in the replacement table for the machine type which is distinguished by the machine type distinction means.

The processing apparatus further includes a setting information storage means which can store setting information which regulates the content of image processing for each purpose of endoscopic examination. The processing apparatus also includes an image processing means for performing image processing on the image produced by the faithful-color-reproduced image production means by referring to a set of setting information selected based on a selection signal input to the processing apparatus among the setting information stored in the setting information storage means. The expression "store for each purpose of endoscopic examination" refers to storing information for each observation region, each test agent which is used for examination, each examination target which should be detected by examination, or the like.

The setting information stored in the setting information storage means includes the following information, for example. When the image processing means includes a plurality of processing units which performs different kinds of image processing from each other, such as brightness level adjustment, sharpness adjustment or hue adjustment, information which specifies at least one of the plurality of processing units as a processing unit which performs processing should be stored as the setting information. Further, a data storage means which can store data which is referred to by the image processing means may be provided, and information which specifies at least a set of data as data which is used for processing among the data stored in the data storage means may be stored as setting information. The data which is used for processing includes all kinds of data which is used for processing, such as a lookup table or a parameter which represents a processing condition.

In the electronic endoscope apparatus which is configured as described above, the faithful-color-reproduced image production means produces images which do not depend on the color obtainment methods of the CCD's, and the image processing means performs image processing on the images produced thereby. Therefore, even if the color obtainment methods of the CCD's are different from each other, the results of image processing are not different from each other. Further, since image processing is performed by using the setting information which has been stored in advance for each purpose of examination, it is not necessary for the users to perform complex adjustment processing at each examination. Therefore, image processing is not burdensome to the users. Further, since image processing is performed on the images produced by the faithful-color-reproduced image production means, it is not necessary to prepare the setting information for each endoscope.

BRIEF DESCRIPTION OF THE DRAWINGS

FIG. 4 is a flow chart illustrating the outline of processing performed by a microcomputer 42;

FIG. 5 is a diagram for explaining processing for converting data to 10-bit data;

FIG. 6 is a diagram illustrating an example of a three-dimensional lookup table which is used by a standard image production unit;

FIG. 7 is a diagram illustrating another example of a three-dimensional lookup table which is used by the standard image production unit;

FIG. 8 is a diagram for explaining a method for processing values which are not in a lookup table;

DESCRIPTION OF THE PREFERRED EMBODIMENTS

As an embodiment of the present invention, an electronic endoscope system which is used for examination of digestive organs will be described below.

1. System Configuration

Figure 1:
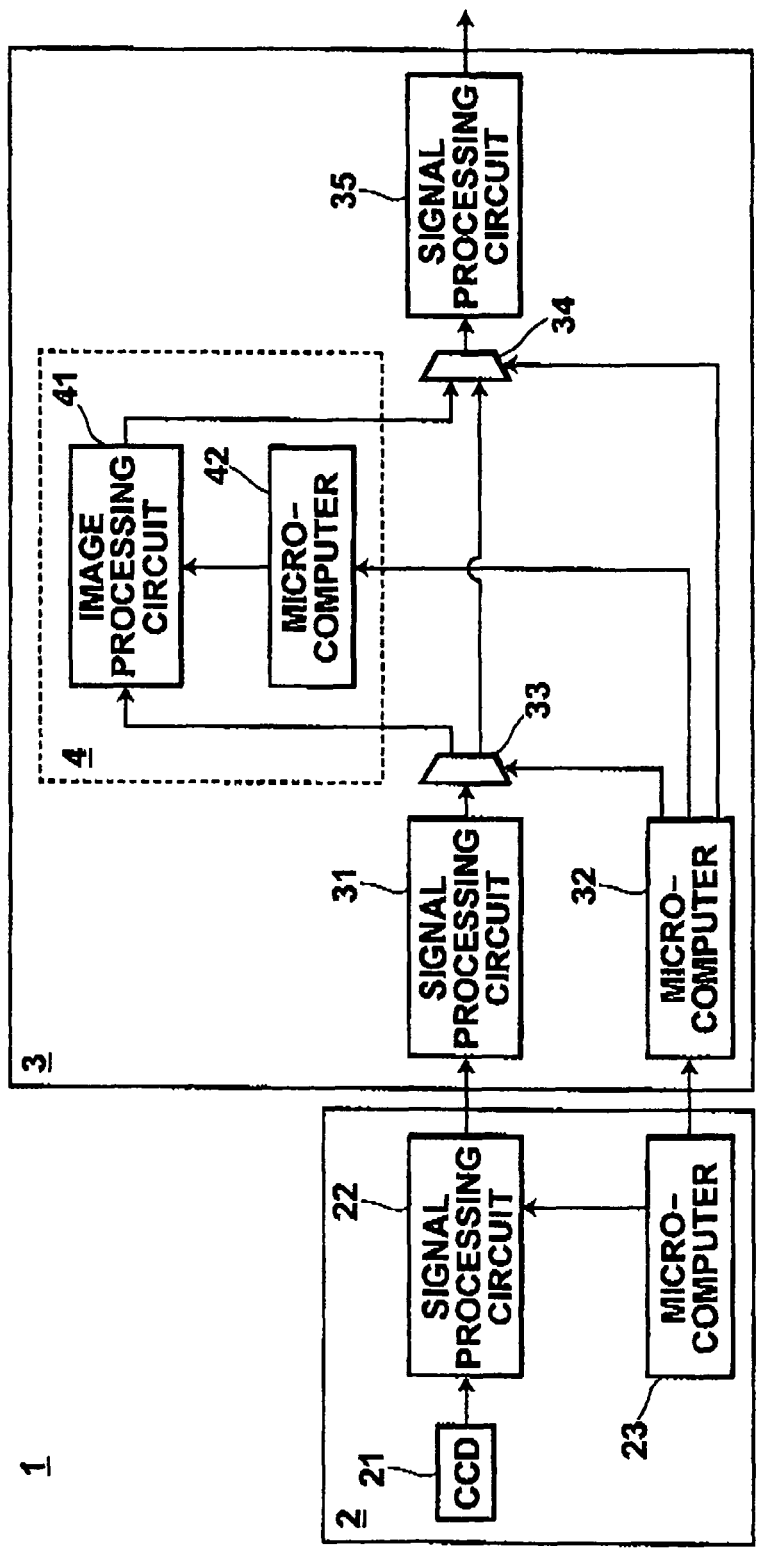
FIG. 1 is a schematic diagram illustrating the configuration of an electronic endoscope system.

FIG. 1 is a schematic diagram illustrating the configuration of an electronic endoscope system. As illustrated in FIG. 1, the electronic endoscope system 1 includes an electronic endoscope 2 (hereinafter, referred to as a scope 2) and a processing apparatus (hereinafter, referred to as a video processor 3) which processes an image obtained by the electronic endoscope. The electronic endoscope system 1 also includes a light source device, monitor, printer, or the like, which are not illustrated. A plurality of kinds of scopes which are appropriate for the purpose of endoscopic examination may be used in the electronic endoscope system 1. In FIG. 1, elements which are common to all of the scopes are illustrated in the scope 2.

The scope 2 includes a CCD (Charge Coupled Device) 21 and a signal processing circuit 22 for processing signals obtained by the CCD 21. The scope 2 also includes a microcomputer 23 which performs various kinds of control processing and a connector unit (not illustrated) which is connected to the video processor 3.

The CCD 21, together with an objective lens, is attached to the leading edge of the scope 2. The CCD 21 obtains light reflected at an observation object, and converts the light into an electric signal. In the present embodiment, the imaging resolution of the CCD is approximately 5 μm.

The signal processing circuit 22 performs signal processing, such as correlated double sampling, automatic gain control, and A/D conversion, on a signal output from the CCD 21. The microcomputer 23 controls the operation of the signal processing circuit 22 and data transfer to the processor 3.

Here, an obtainment method of color information by the scope 2 will be described. Generally, the CCD has a color filter. The CCD obtains information about the color of the observation object by obtaining the light reflected at the observation object through the color filter. Therefore, if the arrangement methods of color filters in CCD's or the kinds of the color filters are different from each other, the quality of obtained color information about images and the color representation of the images are different from each other.

For example, it the CCD's are classified based on the arrangement method of the color filter, CCD's of a plane sequential type and CCD's of a simultaneous type are well known. The CCD's of the plane sequential type obtain information about each color in turn while rotating a rotary filter. The CCD's of the simultaneous type obtain information about all of the colors at once through a mosaic filter. The CCD's of the plane sequential type are used in some conventional scopes, and the CCD's of the simultaneous type are used in some other conventional scopes. However, when the motion of a region which is photographed is faster than the rotation speed of the filter, if the region is photographed by the CCD of the plane sequential type, an image of each color is shifted from that of another color in some cases. Therefore, in the electronic endoscope system 1, a scope including a CCD of the simultaneous type is used as the scope 2.

Further, as the kinds of the color filters, a primary color filter and a complementary color filter are well known. The primary color filter separates light into three color components of red (R), green (G) and blue (B). The complementary color filter separates light into four color components of cyan (C), magenta (M), yellow (Y) and green (G). When an image is obtained by a CCD (hereinafter, referred to as a primary color CCD), in which the primary color filter is provided, the image is represented by RGB. When an image is obtained by a CCD (hereinafter, referred to as a complementary color CCD), in which the complementary color filter is provided, the image is represented by CMYG. Therefore, the conventional electronic endoscope system can use only one of a scope in which the primary color filter is provided and a scope in which the complementary color filter is provided. However, in the electronic endoscope system 1, a plurality of kinds of scopes in which different kinds of color filters are provided may be used.

Table 1 shows examples of scopes which can be used in the electronic endoscope system 1.

TABLE 1

|  | Resolution | CCD | Cut Filter |
| --- | --- | --- | --- |
| Scope A | 650,000 pixels | RGB | None |
| Scope B | 650,000 pixels | RGB | Cut a specific color among reds |
| Scope C | 650,000 pixels | RGB | Cut a specific color among yellows |
| Scope D | 850,000 pixels | RGB | None |
| Scope E | 410,000 pixels | CMYG | None |
| Scope F | 410,000 pixels | CMYG | Cut a specific color among reds |
| Scope G | 180,000 pixels | RGB | Cut a specific color among yellows |
| Scope H | 270,000 pixels | CMYG | None |

In Table 1, a primary color filter is provided in each of the CCD's of the scopes A, B and C, and the resolutions of the scopes A, B and C are the same. However, a cut filter is provided in each of the scopes B and C in addition to the filter provided in the CCD. The cut filter prevents passage of light which has a specific color. As described above, the methods for obtaining the color information about the observation object differ from each other as to whether the CCD is a CCD of a plane sequential type or a CCD of a simultaneous type. The methods also differ from each other as to whether the CCD is a primary color CCD or a complementary color CCD. Further, the methods differ from each other as to the kind of the cut filter which is combined with each CCD.

Next, the configuration of the processor 3 will be described. The processor 3 includes a connector unit, which is not illustrated. The connector unit of the processor 3 is structured so that it can be easily connected to or disconnected from the connector unit in each of the scopes.

Further, the processor 3 includes a signal processing circuit 31. The signal processing circuit 31 produces video signals by performing gamma correction on signals input from the signal processing circuit 22 of the scope 2 through the connector units. If signals output from the signal processing circuit 22 of the scope are CMYG signals, the signal processing circuit 31 also performs processing for converting CMYG signals into RGB signals. Further, the processor 3 includes a microcomputer 32 which controls an operation of the signal processing circuit 31 and communication with the scope 2. Further, a signal processing circuit 35 is arranged after the signal processing circuit 31. The signal processing circuit 35 produces a signal for outputting an image at the monitor by performing pixel number conversion and D/A conversion.

Further, the processor 3 includes a board (circuit board or substrate) 4 specialized in image processing besides a main board (main substrate) on which the signal processing circuit 31, the microcomputer 32 and the signal processing circuit 35 are mounted. An image processing circuit 41 is mounted on the board 4 specialized in image processing. The image processing circuit 41 performs various kinds of image processing on image signals output from the signal processing circuit 31. A microcomputer 42 for controlling the image processing circuit 41 is also mounted on the board 4 specialized in image processing. The image processing circuit 41 is connected to the signal processing circuits 31 and 35 through selectors 33 and 34. The selectors 33 and 34 are switched based on control signals from the microcomputer 32.

Figure 2:
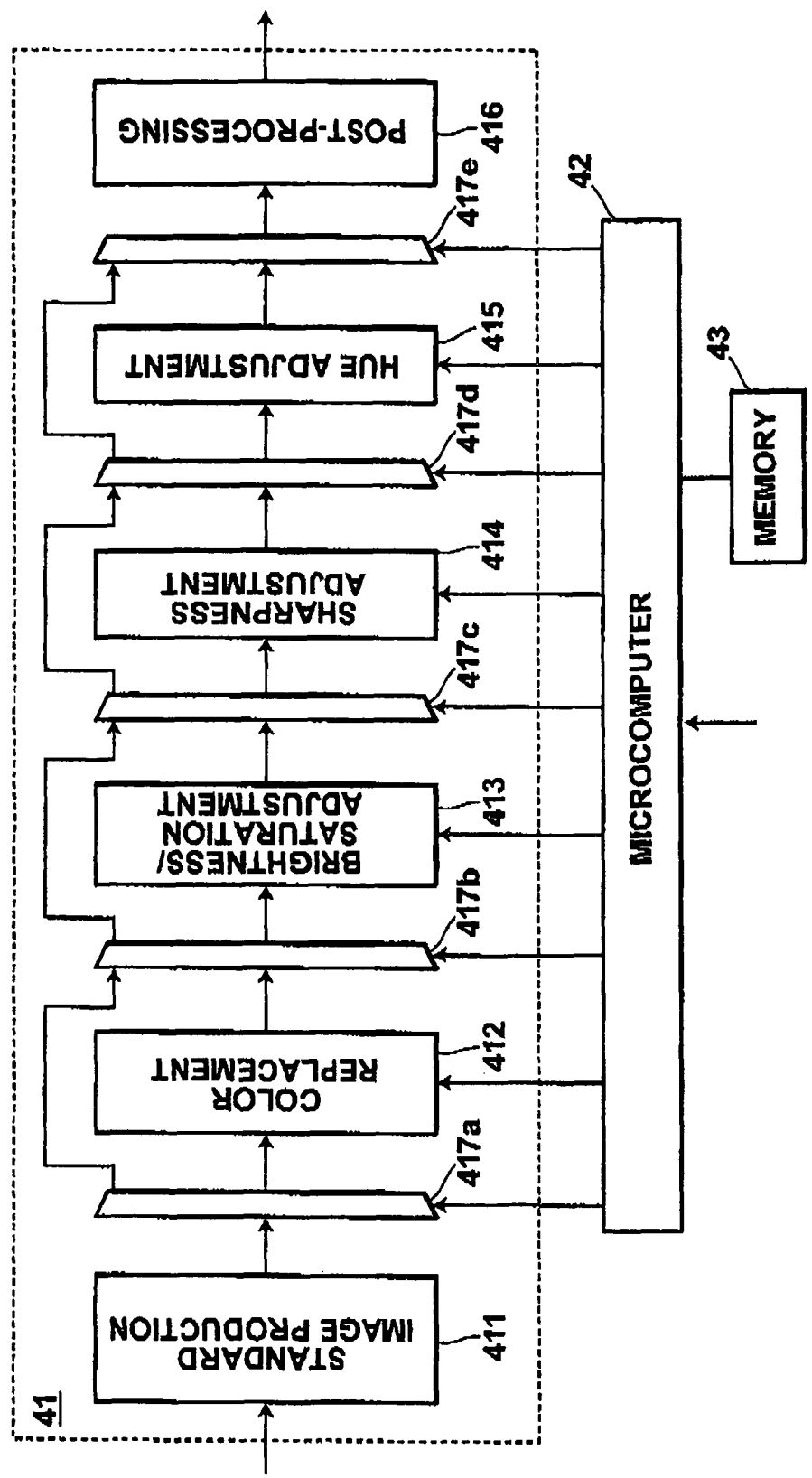
FIG. 2 is a diagram illustrating the configuration of a board (circuit board or substrate) specialized in image processing in detail.

FIG. 2 is a diagram illustrating the configuration of the board 4 specialized in image processing in detail. As illustrated in FIG. 2, the image processing circuit 41 includes six processing units, namely a standard image production unit 411, a color replacement unit 412, a brightness/saturation adjustment unit 413, a sharpness adjustment unit 414, a hue adjustment unit 415, and a post-processing unit 416. It is possible to selectively cause the color replacement unit 412, the brightness/saturation adjustment unit 413, the sharpness adjustment unit 414 and the hue adjustment unit 415 to operate by switching selectors 417a through 417e. The selectors 417a through 417e are switched based on control signals sent from the microcomputer 42.

Further, a memory 43 is mounted on the board 4 specialized in image processing. The memory 43 stores various kinds of lookup tables which are used in processing performed by the color replacement unit 412, the brightness/saturation adjustment unit 413, the sharpness adjustment unit 414, and the hue adjustment unit 415. Among the lookup tables, a lookup table which is used by the color replacement unit 412 is stored for each machine type of the scope. The memory 43 also stores various kinds of parameters for processing. The lookup tables and parameters for processing stored in the memory 43 include those stored in the memory 43 when the electronic endoscope system 1 was shipped from the manufacture thereof and those stored by the user after the electronic endoscope system 1 was purchased by the user. These lookup tables and parameters are referred to by the microcomputer 42, as will be described later.

Here, switching of the selectors 33 and 34 and selectors 417a through 417e will be further described. The user sets, at an operation panel, whether the function of the board 4 specialized in image processing is utilized. When the function of the board 4 specialized in image processing is utilized, the user also sets, at the operation panel, whether each function of the color replacement unit 412, the brightness/saturation adjustment unit 413, the sharpness adjustment unit 414 and the hue adjustment unit 415 is utilized. Information (hereinafter, referred to as setting information) about setting performed by the user at the operation panel is stored in a memory. It is preferable that this memory is provided as a separate memory for storing the setting information. However, a part of the area of the memory 43 or a memory which is provided for other purposes may be used.

This memory can store a plurality of sets of setting information about function selection together. Therefore, the user may select a function at the operation panel whenever he/she uses the electronic endoscope system. Alternatively, setting information for each purpose of examination may be stored in advance, and the user may use the stored information by retrieving it.

The setting information may be stored for each observation region in advance. For example, setting which is appropriate for observation of the stomach or setting which is appropriate for observation of the large intestine may be stored in advance. Alternatively, setting information may be stored for each test agent which is used in the examination. For example, setting which is appropriate for examination using dark blue test agent or setting which is appropriate for examination using reddish brown test agent may be stored in advance. Further, setting information may be stored for each examination target which should be detected in the examination. For example, setting which is appropriate for detection of an aneurysm or setting which is appropriate for detection of a tumor, may be stored in advance.

Figure 3:
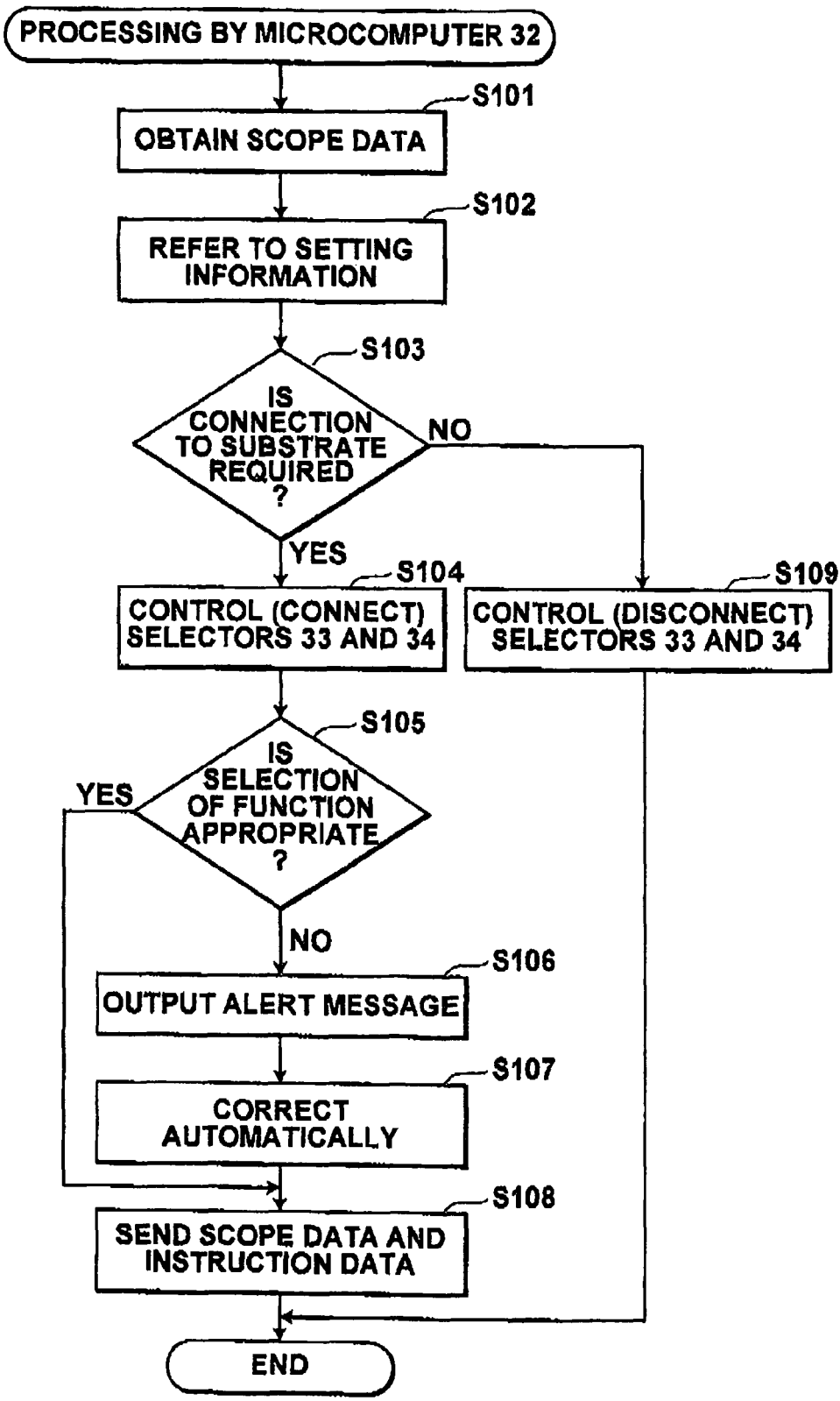
FIG. 3 is a flow chart illustrating the outline of initialization processing performed by a microcomputer 32.

FIG. 3 is a flow chart illustrating the outline of initialization processing performed by the microcomputer 32 when the power source is turned on. When the scope 2 is connected to the processor 3 and the power source of the electronic endoscope apparatus 1 is turned on, the microcomputer 32 communicates with the microcomputer 23 of the scope 2, and obtains data (hereinafter, referred to as scope data) for distinguishing the machine type of the scope 2 (step S101). The scope data includes information illustrated in table 1, namely information representing the resolution of the CCD and the kind of the filter. The information representing the kind of the filter includes information as to whether the filter is a primary color filter or a complementary color filter, whether a cut filter is provided, the frequency (color) which is cut by the cut filter, or the like.

Next, the microcomputer 32 refers to the setting information stored in the memory (step S102). If a plurality of sets of setting information is stored in the memory, the microcomputer 32 refers to setting information which is selected by an operation at the operation panel by the user. When the user performs an operation for selecting the setting information at the operation panel, a selection signal which represents the content of selection is input to the microcomputer 32. The microcomputer 32 judges the selected setting information based on the selection signal input to the microcomputer 32. Then, the microcomputer 32 judges, based on the setting information which the microcomputer 32 has referred to, whether it is necessary to connect the signal processing circuits 31 and 35 to the board 4 specialized in image processing (step S103). The microcomputer 32 controls the selectors 33 and 34 based on the judgment result (steps S104 and S109). If it is not necessary to connect the signal processing circuits 31 and 35 to the board 4 specialized in image processing, and if the board 4 specialized in image processing is disconnected from the signal processing circuits 31 and 35, initialization processing ends.

If the microcomputer 32 controls the selectors so that the board 4 specialized in image processing is connected to the image processing circuits 31 and 35 in step S104, the microcomputer 32 judges, based on the setting information which the microcomputer 32 referred to in step S102, whether the combination of functions selected by the user is appropriate (step S105).

If the microcomputer 32 judges that the combination of the selected functions is appropriate, the microcomputer 32 sends instruction data representing the content of selection to the microcomputer 42 in the board 4 specialized in image processing. The microcomputer 32 sends the instruction data together with the scope data obtained in step S101 (step S108).

Meanwhile, if the microcomputer 32 judges that the combination of the selected functions is inappropriate, the microcomputer 32 outputs an alert message at a monitor (not illustrated) which is connected to the processor 3 (step S106) In this case, the microcomputer 32 automatically corrects the combination of the functions to an appropriate combination (step S107). Then, the microcomputer 32 sends instruction data representing the content of correction to the microcomputer 42 of the board 4 specialized in image processing. The microcomputer 32 sends the instruction data together with the scope data obtained in step S101 (step S108).

After the alert message is output, it is also possible that the scope data and the instruction data is sent only after the user performs a confirmation operation.

The judgment as to whether the function selection is appropriate is made based on a Judgment rule which is stored in advance. Data which defines the judgment rule is stored in advance in the memory provided in the processor 3. The judgment rule is, for example, a rule that the color replacement unit must always operate whenever the brightness/saturation adjustment unit operates. The microcomputer 32 judges whether the selection of functions by the user is appropriate by checking the setting information with the data which defines the judgment rule.

Next, operations of the microcomputer 42 will be described with reference to FIG. 4. When the microcomputer 42 receives the scope data and the instruction data sent from the microcomputer 32 (step S201), the microcomputer 42 distinguishes the machine type of the scope based on the scope data. Further, the microcomputer 42 distinguishes the selected function based on the instruction data (step S202). Then, the microcomputer 42 controls the selectors 417a through 417e so that signals are input to a processing unit which provides the selected function (step S203). Then, the microcomputer 42 retrieves a lookup table or a parameter which is required by each processing unit from the memory 43 (step S204).

As described above, some of the lookup tables are stored for each machine type of the scope. The distinction result of the machine type of the scope is used to select a lookup table which is retrieved from the memory. The retrieved lookup table or parameter is sent to a processing unit in which the lookup table or parameter is required (step S205).

As described above, the processor 3 of the electronic endoscope system 1 performs image processing after the machine type of the scope 2 is distinguished. In other words, the processor 3 performs image processing after the color information obtainment method of the scope is distinguished. Therefore, any kind of scope may be used as the scope 2. In other words, the type of the scope 2 is not limited to a scope in which a complementary color CCD is provided or a scope in which a primary color CCD is provided.

Further, the user can flexibly select an image processing function which she/he wishes to use by performing a predetermined setting operation at the operation panel or by retrieving setting which has been stored in advance. In this case, even if the user selects an inappropriate function because of lack of knowledge or the like, the alert message is output, and an appropriate function is automatically selected. Therefore, the image processing function can be always used effectively.

Further, if a user does not use the function of the board 4 specialized in image processing, he/she can stop input of signals to the board 4 specialized in image processing by performing a predetermined setting operation at the operation panel. Accordingly, it is possible to prevent electric power from being consumed because of unutilized functions.

The image processing circuit 41 may be a circuit on which a plurality of semiconductor apparatuses is arranged. The plurality of semiconductor apparatuses provide functions of the standard image production unit 411, the color replacement unit 412, the brightness/saturation adjustment unit 413, the sharpness adjustment unit 414, the hue adjustment unit 415 and the post-processing unit 416, respectively. Alternatively, the image processing circuit 41 may be a circuit on which a CPU (central processing unit) specialized in image processing and a memory which stores six kinds of image processing programs are arranged. In the image processing circuit 41, whether each processing is performed may be switched in each of the programs.

2. Image Processing Function of System

Image processing performed in the image processing circuit 41 will be described below in detail. Image processing functions provided by the image processing circuit 41 may be largely classified into two kinds of functions.

The first function is a function of absorbing the difference in the color information obtainment method of the scope. Specifically, the difference in the color information obtainment method is absorbed by producing a standard image which does not depend on the machine type of the scope. In other words, the difference in the color information obtainment method is absorbed by producing a standard image which does not depend on the kind of the color filter of the CCD. The standard image is produced by the standard image production unit 411 so that the color of a photographed region is faithfully reproduced.

The second function is a function of processing the standard image produced by the first function so that the standard image becomes appropriate for diagnosis. The second function is provided by the color replacement unit 412, the brightness/saturation adjustment unit 413, the sharpness adjustment unit 414, and the hue adjustment unit 415.

The color replacement unit 412 performs image processing so that the color of the image satisfies the taste of the user. The brightness/saturation adjustment unit 413 performs image processing so that a dark unclear area of the image becomes clearly recognized. The sharpness adjustment unit 414 performs image processing so that structures (for example, projections/depressions or blood vessels) which are necessary for diagnosis are enhanced. Further, the hue adjustment unit 415 performs image processing so that the difference in colors which are necessary for diagnosis is enhanced. The hue adjustment unit 415 also performs image processing so that the difference in colors which are not necessary for diagnosis or so that the difference in colors which prevents correct diagnosis is reduced. The post-processing unit 416 performs processing for removing noises and processing for producing a signal for outputting information at the monitor.

An example of processing performed by each unit will be specifically described.

2.1 Standard Image Production Unit

The standard image production unit 411 is a processing unit which produces a standard image. The standard image production unit 411 performs predetermined preprocessing before producing the standard image. First, the preprocessing will be described.

As described above in the explanation of the signal processing circuit 31, in the electronic endoscope system 1, if the scope 2 includes a complementary color CCD, CMYG signals are converted into RGB signals at the signal processing circuit 31. Specifically, the signal processing circuit 31 converts signals obtained by the complementary color CCD into luminance signals Y and chrominance signals (color difference signals) Cr and Cb. The luminance signals Y and the chrominance signals Cr and Cb (hereinafter, referred to as YCC signals) are further converted into primary color signals R, G and B.

Therefore, there is a possibility that each value of an RGB signal input to the image processing circuit 41 includes a value of a decimal fraction. It a value including a decimal fraction is used in complex calculation, an error due to rounding off may be caused in the result of calculation while calculation for image processing is repeated. Hence, there is a possibility that the error is represented as a difference in color.

Therefore, first, the standard image production unit 411 performs processing for converting 8-bit data into 10-bit data. Specifically, an area corresponding to 10 bits is prepared for each value of R, G and B for each pixel of the image, and a value obtained by multiplying the 8-bit data by 4 is stored in the area for 10 bits. As illustrated in FIG. 5, this operation is performed by shifting the value of 8-bit data by 2 bits to the higher place and storing the shifted value in the area for 10 bits. Then, "0" is stored in the lowest two places of the area. Accordingly, it is possible to increase the effective places for calculation. Therefore, the error caused by rounding off can be reduced. The data converted into 10-bit data by the standard image production unit 411 is reconverted into 8-bit data at the post-processing unit 416, and output at the monitor.

Next, processing for producing a standard image based on the 10-bit data will be described.

A standard image is produced by converting (replacing) RGB data which has been converted into 10-bit data. The RGB data of 10 bits is converted by using a three-dimensional lookup table 5 (hereinafter, referred to as three-dimensional LUT 5) which has been produced in advance.

As illustrated in FIG. 6, the three-dimensional LUT 5 is a table for replacing the values (R, G and B) of colors obtained by the scope with the values (R', G' and B') of actual colors. The values of colors which may be obtained by the scope can be obtained by actually observing each region of a human body with the scope. Further, the values of actual colors can be obtained by measuring the color of each region of a human body with a measuring system during surgery. Therefore, a three-dimensional LUT 5 for the scope can be produced by correlating both data for the same region.

If data is collected by performing observation for each machine type of the scope, a three-dimensional LUT 5 for each machine type can be produced. If the three-dimensional LUT 5 which is produced as described above is used, it is possible to absorb not only the difference in the color information obtainment method of the scope but also difference in other elements besides the color. For example, a difference in the aberration of an objective lens may be absorbed.

The three-dimensional LUT 5 for each machine type, which is produced as described above, is stored in the memory 43 illustrated in FIG. 2. The three-dimensional LUT 5 is provided for the standard image production unit 411 by the microcomputer 42 as described above with reference to FIG. 4. The standard image production unit 411 produces a standard image in which the true colors of the observation object are faithfully reproduced by replacing the R, G and B values of each pixel of the image by using the three-dimensional LUT 5.

The three-dimensional LUT 5 is used to replace data which represents each of R, G and B values in 10 bits with data which represents each of R, G and B values in 10 bits. In the three-dimensional LUT 5, $1024^3$ correspondences are stored. Further, since the three-dimensional LUT 5 must be stored for each machine type of the scope, a plurality of LUT's 5 must be prepared. Hence, it is necessary that the capacity of the memory 43 is sufficiently large to store the three-dimensional LUT's 5.

If the capacity of the memory is limited, only a part of the correspondences may be stored in each of the LUT's, and correspondences other than the stored correspondences may be obtained by performing interpolation calculation. For example, as illustrated in FIG. 7, only correspondences when each of the values of R, G, and B is one of 0, 32, 63, 96, ..., 255 (every 32nd value) are stored in a three-dimensional LUT 6.

If RGB values which are not stored in the three-dimensional LUT 6 are input, coordinate points A through H are extracted from the vicinity of a coordinate point P (r, g, b) of the input value in the RGB space, as illustrated in FIG. 8. Correspondences regarding the coordinate points A through H are stored in the three-dimensional LUT 6. Then, the RGB values of the coordinate points A through H are replaced with R'G'B' values of coordinate points A' through H' based on the three-dimensional LUT 6.

Then, the R'G'B' values of the coordinate points A' through H' are weighted based on the relationship between each of the coordinate points A through H and the coordinate point P, and added. Accordingly, although a correspondence regarding the coordinate point P (r, g, b) is not stored in the three-dimensional LUT 6, a coordinate point P' (r', g', b') which corresponds to the coordinate point P (r, g, b) can be obtained.

A standard image which does not depend on the machine type of the scope, and in which the true colors of the actual object is faithfully reproduced, can be obtained by performing the processing as described above. Image processing after production of the standard image is performed by using the standard image as a processing object. Therefore, the quality of images output from the image processing circuit 41 is not influenced by the machine type of the scope. In other words, even if the machine type of the scope is different from each other, the quality of the images output from the image processing circuit 41 is the same.

In the present embodiment, processing performed by the color replacement unit and other processing units after the color replacement unit may be suppressed by switching the selectors 417a through 417e. Accordingly, the standard image produced by the standard image production unit 411 can be output at the monitor.

2.2. Color Replacement Unit

The color replacement unit 412 performs color replacement processing so that the color of the image satisfies the taste of the user.

For example, a xenon lamp is often used as a light source of the electronic endoscope system. However, when an electronic endoscope was introduced, a halogen lamp was used as the light source. Images obtained by the electronic endoscope using the halogen lamp had yellowish colors. Therefore, a considerable number of users think that they can diagnose patients more accurately using images which have accustomed colors than images in which the colors of the actual object are faithfully reproduced. Therefore, the color replacement unit 412 replaces the colors of the standard image with colors desired by the user so as to satisfy the need of the user as described above.

A three-dimensional LUT is also used to replace the colors in a similar manner to the processing for producing the standard image. The three-dimensional LUT which is used to replace the colors is a table for replacing RGB values of the standard image with R'G'B' values of colors desired by the user. This table may be provided by a manufacturer of the electronic endoscope system 1. Alternatively, the table may be produced by the user.

The three-dimensional LUT which is used by the color replacement unit 412 is also stored in the memory 43 illustrated in FIG. 2. The three-dimensional LUT is sent from the microcomputer 42 to the color replacement unit 412 through the process as described above with reference to FIG. 4. The setting information includes information which is necessary for selection of the table. If a plurality of three-dimensional LUT's is stored in the memory 43, a table is selected based on the setting information, and the selected table is sent to the color replacement unit 412. The color replacement unit 412 converts the RGB values of each pixel which forms the standard image by using the three-dimensional LUT which is sent from the microcomputer 42.

Here, only a part of correspondences may be stored in the three-dimensional LUT in a similar manner to processing for producing standard images. If correspondences regarding some RGB values are not in the three-dimensional LUT, the RGB values may be converted by performing interpolation calculation.

2.3. Brightness/Saturation Adjustment Unit

The brightness/saturation adjustment unit 413 performs processing for adjusting the brightness level of the image. Specifically, the brightness/saturation adjustment unit 413 performs image processing so as to solve a problem caused by a substantial difference in lightness/darkness within the image.

For example, when an image of a region at the opening to the duodenum is obtained by an endoscope, a difference in lightness/darkness is large between the front portion (on the stomach side) and the back portion (in the duodenum). Especially, when an image is obtained by the endoscope after dark test agent such dark blue test agent is distributed, there is a problem that the image of the inside of the duodenum is too dark, and it is impossible to observe the duodenum. It is necessary for diagnosis to obtain an image in which all the area of the image, including the front portion through the back portion, can be clearly recognized even if the test agent is distributed. However, unlike ordinary photography, it is impossible to adjust the position or direction of lighting during endoscopy. Further, it is impossible to increase the intensity of the light of the lighting because if the intensity is too high, the human body may be burned. Therefore, it is necessary to adjust the brightness level of the image by image processing so as to obtain an image which has an appropriate brightness level.

The CCD is an element which controls output electric power based on the amount of light. Since when a dark region is photographed, the output electric power is small, the color information of the region may not be obtained accurately. In this case, if the value of the luminance component of the image is simply increased by image processing, there is a problem that dark blue is not changed to light blue but to green. Therefore, when the brightness/saturation adjustment unit 413 performs processing, the brightness/saturation adjustment unit 413 does not simply adjust the brightness of the image. The brightness/saturation adjustment unit 413 adjusts the brightness level while adjusting the color of the image.

Figure 9:
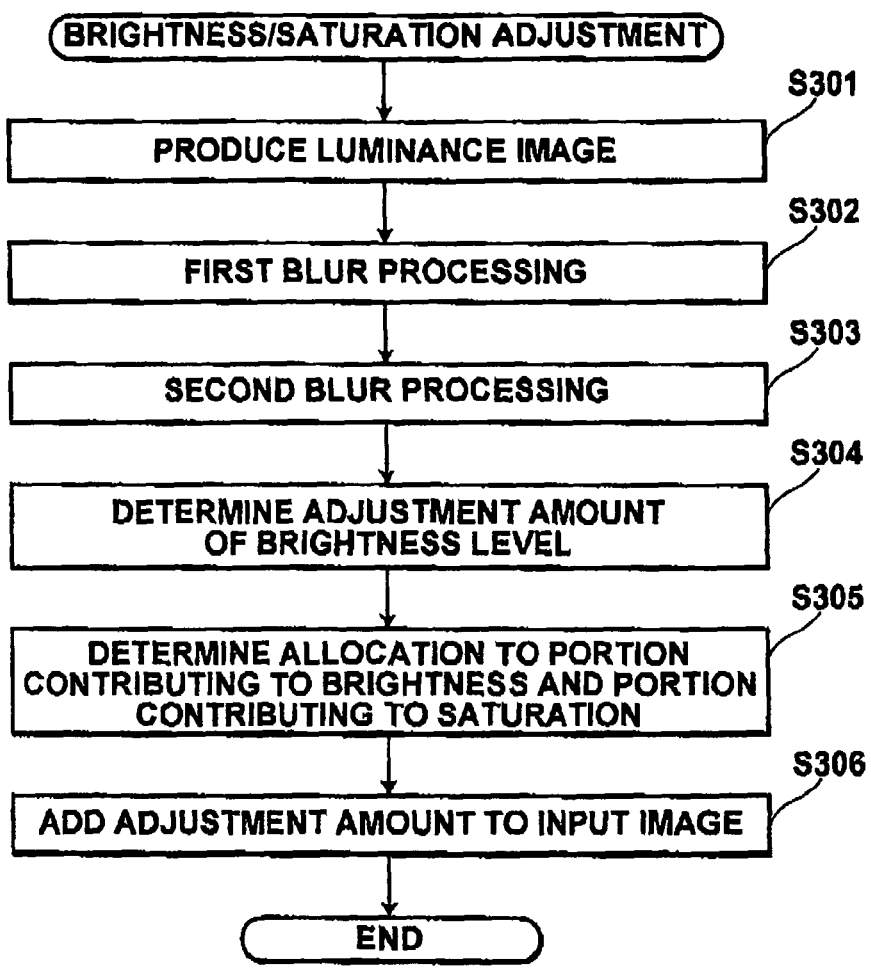
FIG. 9 is a flow chart illustrating the outline of processing performed by a brightness/saturation adjustment unit.

FIG. 9 is a flow chart illustrating the outline of processing performed by the brightness/saturation adjustment unit 413. First, the brightness/saturation adjustment unit 413 converts an input image into YCC signals, and produces a luminance image Y which includes only luminance components (step S301). In the following description, the position of each pixel which forms the image is represented by (x, y), and the value of a pixel at position (x, y) of an image I is represented by I(x, y).

Then, the brightness/saturation adjustment unit 413 performs blur processing on the luminance image Y using a filter for image processing, and produces a luminance blur image UY. Blur processing is performed in two steps. In the first blur processing, a moving-average filter is used as the filter for image processing (step S302). In the second blur processing, a Gaussian filter is used as the filter for image processing. The brightness/saturation adjustment unit 413 produces the luminance blur image UY which represents the distribution of luminance of the image by performing the two steps of blur processing (step S303).

Next, the brightness/saturation adjustment unit 413 determines an adjustment amount of a brightness level, which represents the degree of adjustment of the brightness level (step S304). The adjustment amount of the brightness level is determined for each pixel by converting each pixel value of the luminance blur image UY based on a lookup table LUTy.

Figure 10:
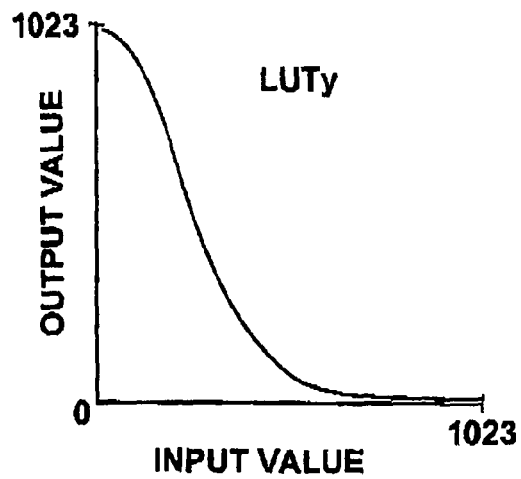
FIG. 10 is a diagram illustrating an example of a lookup table LUTy which is used by the brightness/saturation adjustment unit.

The lookup table LUTy is a one-dimensional lookup table in which correspondences between input values within the range of 0 through 1023 and output values within the range of 0 through 1023 are stored. For example, a table as illustrated in FIG. 10 is used as the lookup table LUTy. In the table illustrated in FIG. 10, if the input value exceeds a predetermined value, the output value becomes 0. In FIG. 10, the correspondences between the input values and the output values are illustrated by using the vertical axis and the horizontal axis. The vertical axis represents the input values, and the horizontal axis represents the output values in FIG. 10.

The lookup table LUTy should be appropriately designed based on the policy for adjusting the brightness level. For example, the table illustrated in FIG. 10 is designed based on a policy that only a dark portion of an image should be lightened without changing the brightness level of a light portion of the image. However, there are various kinds of adjustment policies such as a policy that a dark portion is greatly lightened and a light portion is slightly lightened or a policy that the brightness level of the light portion is slightly suppressed. The lookup table LUTy is stored in the memory 43 illustrated in FIG. 2. The lookup table LUTy is sent from the microcomputer 42 to the brightness/saturation adjustment unit 413 through the process as described above with reference to FIG. 4.

Next, an allocation of the adjustment amount of the brightness level to a portion contributing to brightness and an allocation of the adjustment amount of the brightness level to a portion contributing to saturation are determined (step S305). The allocations of the adjustment amount of the brightness level are determined for each pixel which forms the image. Specifically, rate 1 which is a portion contributing to brightness and rate 2 which is a portion contributing to saturation are determined based on the following equations:

$$Yp(x,y)=Y(x,y)+\mathrm{LUT}y(UY(x,y))$$

$$\mathrm{rate\ 1}(x,y)=\mathrm{LUT}y(UY(x,y))\times\mathrm{LUT}r(Yp)$$

$$\mathrm{rate\ 2}(x,y)=\mathrm{LUT}y(UY(x,y))\times(1-\mathrm{LUT}r(Yp)),$$

where Yp is an estimated value of the luminance value of each pixel when adjustment is performed based only on the luminance information obtained from the luminance blur image UY.

Figure 11:
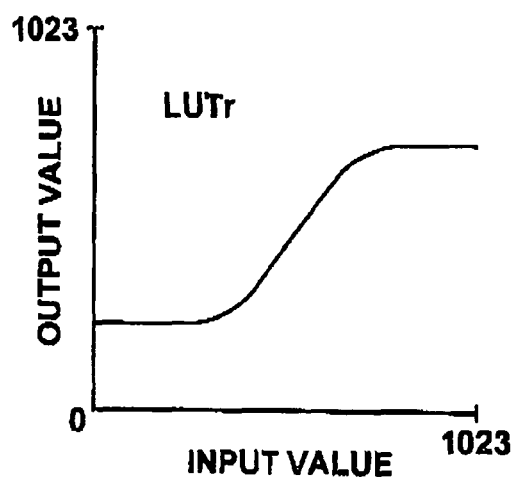
FIG. 11 is a diagram illustrating an example of a lookup table LUTr which is used by the brightness/saturation adjustment unit.

The lookup table LUTr is, for example, a table illustrated in FIG. 11. In the table illustrated in FIG. 11, the output values are substantially constant when the input values are less than or equal to a predetermined value or when the input values are higher than or equal to a predetermined value. When the input values are in the remaining range, the output value increases as the input value increases. This table is designed based on a policy that the effect of a saturation adjustment function should be particularly achieved in a dark region. The lookup table LUTr should be appropriately designed based on the adjustment policy in a similar manner to designing of the lookup table LUTy. The lookup table LUTr is also stored in the memory 43. The lookup table LUTr is sent from the microcomputer 42 to the brightness/saturation adjustment unit 413 through the process as described above with reference to FIG. 4.

As the above equations show, the rate 1 (x, y) and the rate 2 (x, y) are determined so that the total of the rate 1 and rate 2 is equal to the adjustment amount of the brightness level LUTy (UY (x, y)) which is determined in step S304. Further, the allocation to the rate 1 (x, y) and the allocation to the rate 2 (x, y) depend on the estimated luminance value. Specifically, the adjustment amount of the brightness level is determined by performing conversion based on the lookup table LUTy. Then, the degree of adjustment of saturation is further determined within the determined amount. Further, when the degree of adjustment of saturation is determined, an estimated value obtained by assuming that the saturation is not adjusted but only the brightness is adjusted is referred to.

Next, the brightness/saturation adjustment unit 413 adds an adjustment value of saturation and an adjustment value of brightness to the RGB value of each pixel (x, y) which forms an input signal according to the following equations:

$$R'(x,y)=R(x,y)+Y(x,y)\times\mathrm{rate\ 1}+R(x,y)\times\mathrm{rate\ 2}$$

$$G'(x,y)=G(x,y)+Y(x,y)\times\mathrm{rate\ 1}+G(x,y)\times\mathrm{rate\ 2}$$

$$B'(x,y)=B(x,y)+Y(x,y)\times\mathrm{rate\ 1}+B(x,y)\times\mathrm{rate\ 2}.$$

The adjustment value of saturation is obtained by weighting the RGB value based on the portion contributing to saturation. The adjustment value of brightness is obtained by weighting the pixel value of the luminance image based on the portion contributing to brightness (step S306).

Alternatively, the adjustment value of brightness may be obtained by weighting the pixel value of the luminance blur image based on the portion contributing to brightness. In other words, processing in step S306 may be performed based on the following equations:

$$R'(x,y)=R(x,y)+UY(x,y)\times\mathrm{rate\ 1}+R(x,y)\times\mathrm{rate\ 2}$$

$$G'(x,y)=G(x,y)+UY(x,y)\times\mathrm{rate\ 1}+G(x,y)\times\mathrm{rate\ 2}$$

$$B'(x,y)=B(x,y)+UY(x,y)\times\mathrm{rate\ 1}+B(x,y)\times\mathrm{rate\ 2}.$$

When the brightness level is adjusted using the above equations, the saturation as well as the luminance is adjusted. Therefore, an image which has natural colors, in other words, a natural image can be obtained. For example, when processing is performed using the lookup tables illustrated in FIGS. 10 and 11, adjustment of saturation is carefully performed particularly on the dark region. Therefore, an image is reproduced so that even fine-detail structures in the dark region are easily recognized. Alternatively, the lookup table may also be designed so that the dark region is not changed because the dark region is unnecessary for diagnosis and only a region which is necessary for diagnosis is processed so that fine-detail structures in the region are easily recognized. As described above, the brightness level can be adjusted by using a method which is appropriate for the purpose of the image, and the brightness level can be adjusted by an amount which is appropriate for the purpose.

Here, blur processing in steps S302 and S303 will be further described.

A method for producing a blur image of an image by replacing the value of each pixel which forms the image with a value obtained by performing operations using a filter for image processing is well known. In the method for producing the blur image, as described above, a filter for image processing, which has a size of approximately 3×3 pixels through 15×15 pixels, is normally used to perform operations. However, the brightness/saturation adjustment unit 413 performs an operation using a filter for image processing, which has a width of the one-fourth of that of the image or wider. For example, if the width of the image is 1024 pixels, a filter which has a size of 255×255 pixels or larger is used as the filter for image processing.

Figure 12A:
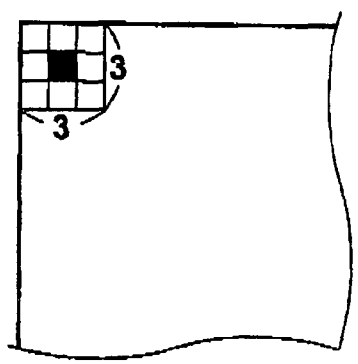
FIG. 12A is a diagram for explaining a relationship between the size of a filter for image processing and the result of processing.
Figure 12B:
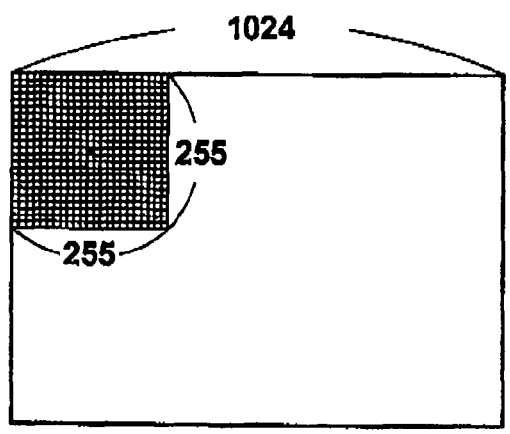
FIG. 12B is a diagram for explaining a relationship between the size of filter for image processing and the result of processing.

FIGS. 12A and 12B are diagrams for explaining relationship between the size of a filter for image processing and the result of processing. FIG. 12A is a diagram illustrating an example of normal image processing. FIG. 12B is a diagram illustrating an example of image processing performed by the brightness/saturation adjustment unit 413.

As illustrated in FIG. 12A, if a filter for image processing, which has a size of 3×3 pixels is used, the value of each pixel depends on the values of nine pixels. Meanwhile, if a filter for image processing, which has a size of 255×255 pixels is used, the value of each pixel depends on the values of $255^2$ pixels.

When the brightness level of an image in which a large difference in lightness/darkness is present is adjusted, it is not appropriate to simply lighten a dark region. The difference in lightness/darkness should be kept so that the image does not become an unnatural image. Specifically, the dark region should be lightened while the balance of the brightness level of the whole image is kept. Therefore, when the brightness level of a pixel is determined, it is necessary that the brightness level of the pixel is determined by referring to the values of pixels which are far from the pixel as well as the values of pixels in the vicinity of the pixel.

For example, the value of each pixel of a luminance blur image produced using a filter for image processing, which has a small size as illustrated in FIG. 12A, is determined independently of the values of pixels which are apart from the pixel by 100 pixels or more. Therefore, there is a possibility that the relationship in lightness/darkness between the pixel and some of the pixels which are apart from the pixel by 100 pixels or more may be reversed.

In contrast, the value of each pixel of the luminance blur image which is produced using a filter for image processing, which has a large size as illustrated in FIG. 12B, is determined by referring to the values of pixels which are apart from the pixel by 100 pixels or more. Therefore, there is no possibility that the relationship in lightness/darkness between the pixel and some of the pixels which are apart from the pixel by 100 pixels or more is reversed. Hence, the balance of lightness/darkness in the whole image can be kept.

In the processing performed by the brightness/saturation adjustment unit 413, the luminance blur image UY is used to calculate the estimated luminance and to determine the portion contributing to brightness and the portion contributing to saturation. The luminance blur image UY is an image in which the balance of lightness/darkness in the whole image is faithfully reflected. Therefore, an image after adjustment is a natural image in which the balance of lightness/darkness is kept.

Here, if the size of the filter for image processing is large, the operation amount is naturally large. However, since image processing of the electronic endoscope must be performed in real-time unlike image processing of an X-ray apparatus, or the like, it is not desirable that processing time becomes long.

Therefore, when the brightness/saturation adjustment unit 413 performs the first blur processing in step S302, operations are performed by placing the filter at every few pixels in both vertical and horizontal directions. Accordingly, the operation amount is reduced. For example, if the operation is performed at every three pixels, the operation amount can be reduced to 1/9 of that of the operation performed on all of the pixels of the image. Accordingly, processing time can be reduced.

The brightness/saturation adjustment unit 413 may also perform the second blur processing at every few pixels in a similar manner to that of the first blur processing. However, when an operation is performed using a Gaussian filter, there is a possibility that an artifact is created if the processing is performed at every few pixels. Therefore, it is preferable that the operation in the first blur processing is performed at every few pixels, and the operation in the second blur processing is performed on all of the pixels in the image.

2.4 Sharpness Adjustment Unit

The sharpness adjustment unit 414 performs image processing mainly to enhance the sharpness of the image. Since an image obtained by the endoscope does not include sharp edges, the sharpness adjustment unit 414 performs processing mainly to enhance the structure of the observation object, such as projections/depressions of the mucous membrane and blood vessels.

For example, if some swelling is formed under the mucous membrane of the stomach, thin blood vessels form spirals, and thick blood vessels are curved. Therefore, it is extremely important to observe the change in the shape of the blood vessels to find a hidden lesion. However, the color of the inside of the stomach is substantially the same through the entire area of the stomach. Therefore, if a user tries to distinguish the blood vessels based on the frequency components of the image, it is impossible to distinguish the thick blood vessels from the shadow of a swelling.

Therefore, the sharpness adjustment unit 414 performs sharpness adjustment processing while considering the color of the image.

Figure 13:
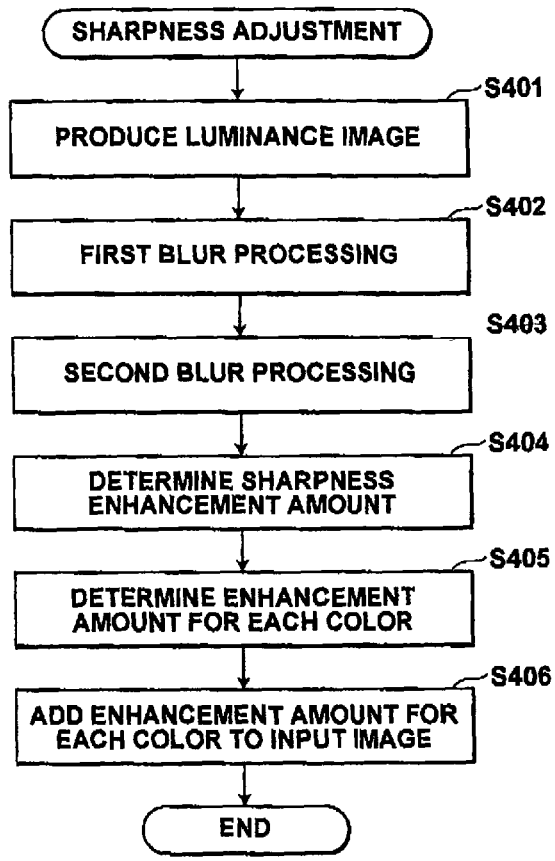
FIG. 13 is a flow chart illustrating the outline of processing performed by a sharpness adjustment unit.

FIG. 13 is a flow chart illustrating the outline of processing performed by the sharpness adjustment unit 414.

First, the sharpness adjustment unit 414 converts an input signal into a YCC signal, and produces a luminance image Y(x, y) including only luminance components (step S401).

Then, the sharpness adjustment unit 414 performs blur processing on the luminance image Y(x, y) using a filter for image processing, and produces a luminance blur image U(Y (x, y)). The blur processing is performed in two steps. In the first blur processing, a moving-average filter is used as the filter for image processing (step S402). If the filter is too small, information about a relatively large structure such as a projection/depression on the stomach wall is not included. Therefore, a filter which has a size of approximately 80×80 pixels is used. Further, in step S402, operations are performed at every few pixels so as to reduce the operation amount in a manner similar to the processing performed by the brightness/saturation adjustment unit 413 in step S302.

In the second blur processing, a Gaussian filter is used as a filter for image processing (step S403). As the Gaussian filter, three kinds of filters which have different standard deviations are used.

Figures 14A, 14B, 14C:
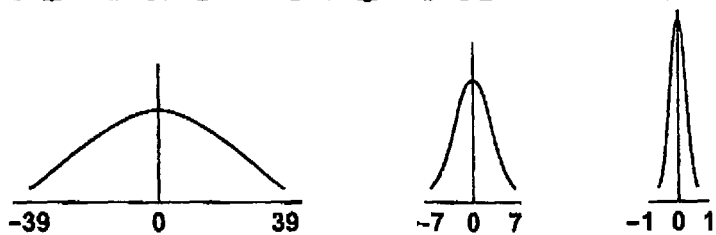
FIG. 14A is a diagram illustrating an example of a Gaussian filter which is used by the sharpness adjustment unit.
FIG. 14B is a diagram illustrating another example of a Gaussian filter which is used by the sharpness adjustment unit.
FIG. 14C is a diagram illustrating another example of a Gaussian filter which is used by the sharpness adjustment unit.

FIGS. 14A, 14B and 14C are diagrams illustrating three kinds of Gaussian filters. In each of FIGS. 14A, 14B and 14C, the horizontal axis represents the position of each pixel when the position of the central pixel of the filter for image processing is 0. The vertical axis represents the value of each pixel which forms the filter. FIG. 14A is a diagram illustrating a filter which has a largest standard deviation among the three kinds of filters. The filter has a size of 79×79 pixels. If this filter is used, a relatively large structure such as the projection/depression on the inner wall of an organ or an artery can be extracted. Further, FIG. 14B is a diagram illustrating a filter which has a standard deviation lower than that of the filter illustrated in FIG. 14A. The filter has a size of approximately 15×15 pixels. If this filter is used, a medium-sized structure such as blood vessels which have regular thicknesses can be extracted. FIG. 14C is a diagram illustrating a filter which has a standard deviation lower than that of the filter illustrated in FIG. 14B. The filter in FIG. 14C has a size of approximately 3×3 pixels. If this filter is used, a thin structure such as capillary vessels can be extracted.

In step S403, if a Gaussian filter in which a standard deviation is set based on the size of a structure which should be enhanced is used, a luminance blur image UY can be produced so that sufficient image information for distinguishing the structure which should be enhanced remains in the luminance blur image UY.

In the second blur processing, operations may be performed in three steps by using three kinds of Gaussian filters. However, the operation should be performed by using a filter for image processing, which has the functions of all of the three Gaussian filters, so as to reduce processing time.

After the sharpness adjustment unit 414 produces the luminance blur image UY, the sharpness adjustment unit 414 calculates a difference between the value of the luminance image Y and the value of the luminance blur image UY for each pixel based on the following equation:

$$C(x,y)=|Y(x,y)-UY(x,y)|\times LUTy(UY(x,y)).$$

Then, the sharpness adjustment unit 414 determines a sharpness enhancement amount C (x, y) based on the difference value (step S404). The lookup table LUTy may be the same as the lookup table LUTy which is used by the brightness/saturation adjustment unit 413. Alternatively, the lookup table LUTy may be designed based on another adjustment policy.

In general sharpness enhancement processing, the sharpness is enhanced by simply adding the sharpness enhancement amount C(x,Y) as described above to each pixel value of the input image. However, in the processing performed by the sharpness adjustment unit 414, enhancement amount Cr(x, y), Cg(x, y) or Cb(x, y) for each color, which depends on colors, are obtained (step S405). The sharpness is enhanced by adding the enhancement amount for each color to each pixel value of the input image.

The enhancement amount for each color is calculated as follows. First, rate 3 (portion contributing to brightness), which represents a portion contributing to adjustment of brightness in sharpness enhancement, and rate 4 (portion contributing to saturation), which represents a portion contributing to adjustment of saturation in sharpness enhancement, are determined based on the following equations:

$$\text{rate 3}=LUTc(Y(x,y))\times(x,y)$$

$$\text{rate 4}=\{1-LUTc(Y(x,y))\}\times(x,y).$$

As the above equations show, the portion contributing to brightness and the portion contributing to saturation are determined so that the sum of the portion contributing to brightness and the portion contributing to saturation is equal to the sharpness enhancement amount obtained in step S404. LUTc is a table for determining an allocation to the portion contributing to brightness and an allocation to the portion contributing to saturation. The table LUTc may be defined based on the targeted image quality as appropriate.

Next, the enhancement amount for each color is determined based on the following equations:

$$Cr(x,y)=Y(x,y)\times\text{rate 3}+R(x,y)\times\text{rate 4}$$

$$Cg(x,y)=Y(x,y)\times\text{rate 3}+G(x,y)\times\text{rate 4}$$

$$Cb(x,y)=Y(x,y)\times\text{rate 3}+B(x,y)\times\text{rate 4}.$$

Alternatively, the enhancement amount for each color may be determined based on the following equations:

$$Cr(x,y)=C(x,y)\times R(x,y)/Y(x,y)$$

$$Cg(x,y)=C(x,y)\times G(x,y)/Y(x,y)$$

$$Cb(x,y)=C(x,y)\times B(x,y)/Y(x,y).$$

Next, the enhancement amount for each color which was obtained by using one of the sets of equations as described above is added to the input signal, and the sharpness is enhanced as described in the following equations (step S406):

$$R'(x,y)=R(x,y)+Cr(x,Y)$$

$$G'(x,y)=G(x,y)+Cg(x,Y)$$

$$B'(x,y)=B(x,y)+Cb(x,Y).$$

If the sharpness is enhanced by adding the enhancement amount for each color, the sharpness can be enhanced according to the color of the image. In this case, since the color component which is enhanced is different between the thick blood vessels and the shadow of a swelling, the shadow of the swelling is not recognized as a blood vessel by mistake.

As described above, both of the brightness/saturation adjustment unit 413 and the sharpness adjustment unit 414 produce luminance blur images, and use the produced luminance blur images for processing. Therefore, a processing unit for producing a luminance blur image may be provided before the selector 417a illustrated in FIG. 2, and the luminance blur image produced by the processing unit may be input to the brightness/saturation adjustment unit 413 and the sharpness adjustment unit 414. In this case, a filter for image processing, which is used to produce the luminance blur image, is a filter which has two kinds of functions.

The lookup table and the filter for image processing which are used by the sharpness adjustment unit 414 are stored in the memory 43 illustrated in FIG. 2. The lookup table and the filter for image processing are sent from the microcomputer 42 to the sharpness adjustment unit through the process as described above with reference to FIG. 4.

2.5 Hue Adjustment Unit

The hue adjustment unit 415 performs image processing so as to expand a hue which is necessary for diagnosis and to reduce a hue which is not necessary for diagnosis.

In examinations using an endoscope, test agent including dye is distributed to examine the human body in some cases. For example, if dark-blue test agent called Indigo Carmine is distributed on the inner wall of the stomach, the test agent remains in the fold of the mucous membrane. Therefore, the projections/depressions on the stomach wall can be observed as a contrast of red and blue. Further, when dark-blue test agent called Methylene Blue is distributed, only the normal mucous membrane is dyed in blue. However, tumors are not dyed in blue. Therefore, it is possible to recognize whether a tumor is present and the position of the tumor, if the tumor is present.

When the examination as described above is performed, information such as that the tone of the mucous membrane is slightly different in each region is not necessary for diagnosis.

Figure 15:
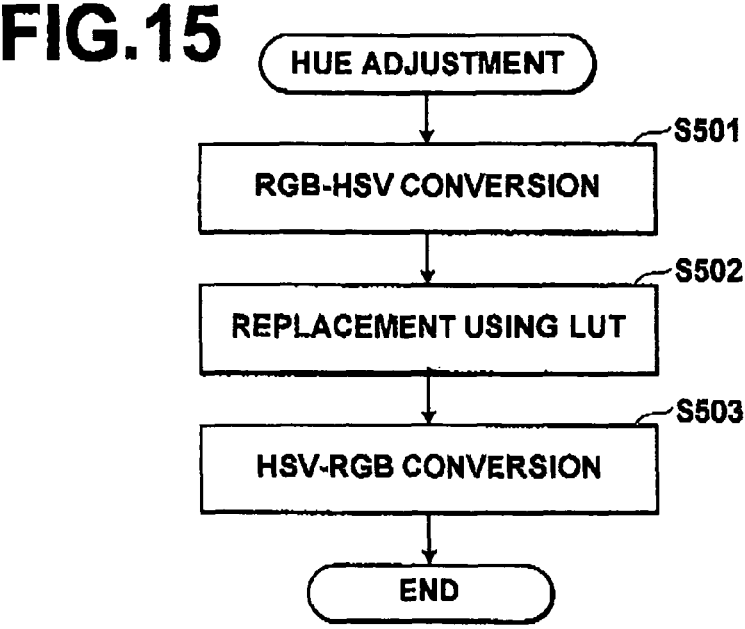
FIG. 15 is a flow chart illustrating the outline of processing performed by a hue adjustment unit.

FIG. 15 is a flow chart illustrating the outline of processing performed by the hue adjustment unit 415. First, the hue adjustment unit 415 converts an RGB signal into an HSV (Hue, Saturation and Value) signal, and extracts only a hue component. Accordingly, the hue adjustment unit 415 produces a hue image which shows the distribution of hues (step S501). Then, the hue adjustment unit 415 converts the value H(x, y) of each pixel which forms the hue image by using a lookup table LUTh (step S502).

The lookup table LUTh is a table which is designed so that the hue is expanded in a range of colors which are necessary for diagnosis, and so that the hue is narrowed in a range of colors which are unnecessary for diagnosis.

Figure 16:
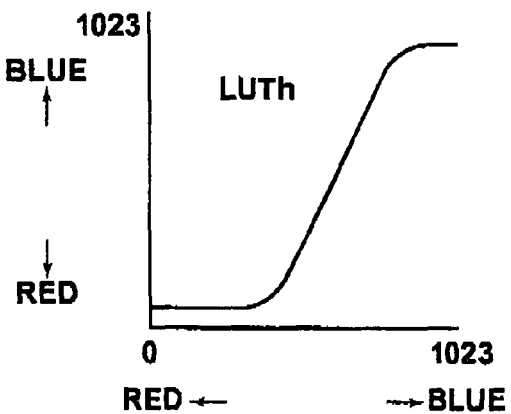
FIG. 16 is a diagram illustrating an example of a lookup table LUTh which is used by the hue adjustment unit.

For example, if the lookup table LUTh illustrated in FIG. 16 is used, blue-purple is replaced with a color which is closer to blue. If image processing is performed using the lookup table LUTh, when photograph is taken after a blue-purple test agent is distributed, it is possible to increase the contrast in color between the portion of the mucous membrane, onto which the test agent is attached, and the portion of the mucous membrane, onto which the test agent is not attached. Further, if the lookup table LUTh illustrated in FIG. 16 is used, all of the colors from red through pink are replaced with pink. Therefore, if image processing is performed by using the lookup table LUTh, a slight difference in reddish colors of the mucous membrane does not appear in the image.

Figure 17:
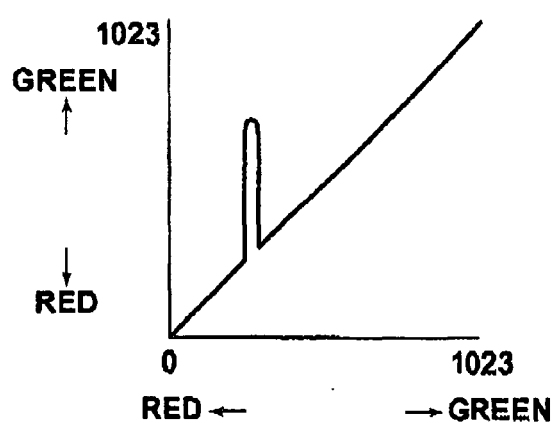
FIG. 17 is a diagram illustrating another example of the lookup table LUTh which is used by the hue adjustment unit.

Further, the lookup table LUTh illustrated in FIG. 17 is a table which replaces only the color of the pigment of hemoglobin with green and which does not replace other colors. This table is designed to produce an image which is appropriate for examination of the blood flow by increasing a difference between the color of the blood and that of the mucous membrane.

All of the colors included in an image obtained by an endoscope are reddish colors. None of the colors of a photography object is blue or green except that of the test agent. Therefore, even if the color of the blood is replaced with green, there is no possibility that the blood is not distinguished from another green object. Hence, in endoscopic image processing, it is possible to perform processing so as to extremely expand the hue, as illustrated in FIG. 17.

After the hue adjustment unit 415 expands or reduces the hue by replacing colors by using the lookup table LUTh in step S502, the hue adjustment unit 415 converts an HSV signal into an RGB signal (step S503). The HSV signal is a signal including hue data H'(x, y), which is obtained by performing conversion using the lookup table LUTh, as a hue component.

It is preferable that a plurality of lookup tables is prepared as the lookup table LUTh. The plurality of lookup tables should be designed based on the idea of a radiologist who is the user of the endoscope, the design policy of the manufacturer of the endoscope, the type of test agent for examination, the region which is examined, the purpose of examination, or the like. The lookup table LUTh may be provided by the manufacturer which supplies the electronic endoscope system 1. Alternatively, the lookup table LUTh may be created by the user of the electronic endoscope system 1. The lookup table LUTh is stored in the memory 43 illustrated in FIG. 2. The lookup table LUTh is sent from the microcomputer 42 to the hue adjustment unit 415 through the process as described above with reference to FIG. 4.

In the above example, the hue is adjusted in HSV space. However, the RGB signal may be converted into a Lab signal, and the Lab signal may be converted into an RGB signal again after the a-component and b-component of the Lab signal are converted by using a lookup table.

Alternatively, it is also possible that an RGB signal is not converted into a signal in other color space. In that case, a three-dimensional LUT may be prepared in a similar manner to the processing performed by the standard image production unit 411 or the color replacement unit 412. Then, the input RGB signal may be directly replaced with an RGB signal which is produced by performing hue adjustment.

An embodiment of the present invention has been described in detail. However, the scope of the present invention should not be limited to the above embodiment, but it should be defined by the claims of the present application.

What is claimed is:

1. An electronic endoscope apparatus comprising: an electronic endoscope, wherein the processing apparatus includes:
   a connection unit capable of selectively connecting a plurality of machine types of electronic endoscopes in which a color space of color information to be obtained is different from each other;
   preprocessing unit configured to receive image data from the electronic endoscope and determine whether color space conversion is necessary to a second standard space;
   a standard space color converter configured to convert image data to the second standard color space when the preprocessing unit determines that the color space conversion is necessary;
   a plurality of replacement tables which are provided for the plurality of machine types of electronic endoscopes respectively, and each of which stores a correspondence between values representing colors which can be obtained by each of the electronic endoscopes by photographing an observation object and values representing the true colors of the observation object that have been obtained by measuring the color of each region of a human body with a measuring system during surgery;
   a machine type distinction mans which distinguishes the machine type of the electronic endoscope connected to the processing apparatus by obtaining information representing the machine type of the electronic endoscope from the electronic endoscope;
   a faithful-color—reproduced image production means which produces an image in which the true colors of the observation object are faithfully reproduced by performing a first phase of image processing that replaces the values of colors obtained by the electronic endoscope connected to the processing apparatus by suing the correspondence stored in the replacement table for the machine type distinguished by the machine type distinction means,
   a setting information storage means which can store setting information regulating the content of a second phase of image processing for each purpose of endoscopic examination, and
   an image processing means which refers to a set of setting information selected based on a selection signal input to the processing apparatus among the setting information stored in the setting information storage means, and which performs the second phase of image processing on the image produced by the faithful-color-reproduced image production means.

2. An electronic endoscope apparatus as defined in claim 1, wherein the setting information storage means can store the setting information for each observation region.

3. An electronic endoscope apparatus as defined in claim 1, wherein the setting information storage means can store the setting information for each test agent which is used for examination.

4. An electronic endoscope apparatus as defined in claim 1, wherein the setting information storage means can store the setting information for each examination target which should be detected by examination.

5. An electronic endoscope apparatus as defined in claim 1, wherein the image processing means includes a plurality of processing units which performs different kinds of image processing from each other, and
 wherein the setting information includes information which specifies at least one of the plurality of processing units, which performs processing.

6. An electronic endoscope apparatus as defined in claim 5, wherein the processing performed by one of the plurality of processing units is processing for adjusting the brightness level of the image.

7. An electronic endoscope apparatus as defined in claim 5, wherein the processing performed by one of the plurality of processing units is processing for adjusting the sharpness of the image.

8. An electronic endoscope apparatus as defined in claim 5, wherein the processing performed by one of the plurality of processing units is processing for adjusting the hue of the image.

9. An electronic endoscope apparatus as defined in claim 1, further comprising a data storage means which can store data which is referred to by the image processing means, wherein the setting information includes information which specifies at least a set of data which is used for processing among the data stored by the data storage means.

* * * * *